United States Patent
Kristensen et al.

(10) Patent No.: US 8,177,767 B2
(45) Date of Patent: May 15, 2012

(54) CARTRIDGE AND MEDICAL DELIVERY SYSTEM ACCOMMODATING SUCH CARTRIDGE

(75) Inventors: Lars Thougaard Kristensen, Tai Po (HK); Lars Korsbjerg Nielsen, Birkerød (DK); Kim Steengaard, Birkerød (DK); Morten Bæk Jensen, Nærum (DK)

(73) Assignee: Novo Nordisk A/S, Bagsvaerd (DK)

( * ) Notice: Subject to any disclaimer, the term of this patent is extended or adjusted under 35 U.S.C. 154(b) by 203 days.

(21) Appl. No.: 12/552,566

(22) Filed: Sep. 2, 2009

(65) Prior Publication Data

US 2010/0004603 A1    Jan. 7, 2010

Related U.S. Application Data

(63) Continuation of application No. 11/784,738, filed on Apr. 9, 2007, now abandoned, which is a continuation of application No. 10/230,428, filed on Aug. 23, 2002, now abandoned.

(60) Provisional application No. 60/317,307, filed on Sep. 5, 2001.

(30) Foreign Application Priority Data

Aug. 27, 2001 (DK) .................................. 2001 01268

(51) Int. Cl.
*A61M 3/00* (2006.01)
*A61B 19/00* (2006.01)

(52) U.S. Cl. ........................................ 604/404; 604/189

(58) Field of Classification Search ............... 604/93.01, 604/181, 187, 200–204, 244, 533–535, 404; 604/189
See application file for complete search history.

(56) References Cited

U.S. PATENT DOCUMENTS

| | | | |
|---|---|---|---|
| 31,873 | A | 4/1861 | Howes |
| 1,594,493 | A | 8/1926 | Brown |
| 2,020,828 | A | 11/1935 | Goldberg |
| 2,707,466 | A | 5/1955 | Hoskins et al. |
| 2,818,864 | A | 1/1958 | Hudson |
| 2,865,372 | A | 12/1958 | Miskel et al. |
| 2,880,723 | A | 4/1959 | Adams |
| 2,888,924 | A | 6/1959 | Dunmire |

(Continued)

FOREIGN PATENT DOCUMENTS

CH        315980        9/1956

(Continued)

OTHER PUBLICATIONS

Novo Nordisk product brochure for Insuject-X (1987).*

(Continued)

*Primary Examiner* — Kevin C Sirmons
*Assistant Examiner* — Andrew M Gilbert
(74) *Attorney, Agent, or Firm* — Wesley A. Nicolas; Marc A. Began; Reza Green

(57) ABSTRACT

A cartridge having a distal end provided with a mechanical coding. The coding has the form of a circular protrusion where the circular outer diameter is dedicated a specific concentration of insulin contained in the cartridge. The distal end of the cartridge is fitted in to a circular contour in the housing. The outer diameter of the protrusion on the distal end of the cartridge is chosen as a larger diameter for a higher concentration of insulin. In this way only a cartridge containing the correct concentration or a lower concentration fits into a delivery system designed for a specific concentration of insulin.

20 Claims, 3 Drawing Sheets

U.S. PATENT DOCUMENTS

| | | | |
|---|---|---|---|
| 3,021,840 | A | 2/1962 | Hallamore et al. |
| 3,130,724 | A | 4/1964 | Higgins et al. |
| 3,130,742 | A | 4/1964 | Higgins et al. |
| 3,170,667 | A | 2/1965 | Szohatzky |
| 3,336,924 | A | 8/1967 | Sarnoff et al. |
| 3,375,825 | A | 4/1968 | Keller |
| 3,820,652 | A | 6/1974 | Thackston |
| 3,831,599 | A | 8/1974 | Needham |
| 3,895,633 | A | 7/1975 | Bertner et al. |
| 3,916,893 | A | 11/1975 | De Felice |
| 3,989,044 | A | 11/1976 | Meierhoefer |
| 4,089,432 | A | 5/1978 | Crankshaw et al. |
| 4,150,673 | A | 4/1979 | Watt |
| 4,280,723 | A | 7/1981 | Moldestad |
| 4,490,142 | A | 12/1984 | Silvern |
| RE31,878 | E | 5/1985 | Howes |
| 4,592,745 | A | 6/1986 | Rex et al. |
| 4,619,640 | A | 10/1986 | Potolsky et al. |
| 4,619,651 | A | 10/1986 | Kopfer et al. |
| 4,664,656 | A | 5/1987 | Taddei |
| 4,685,314 | A | 8/1987 | Greenwalt et al. |
| 4,693,833 | A | 9/1987 | Toshikuni et al. |
| 4,740,205 | A | 4/1988 | Seltzer |
| 4,768,568 | A | 9/1988 | Fournier et al. |
| 4,781,701 | A | 11/1988 | Geprags |
| 4,944,736 | A | 7/1990 | Holtz |
| 4,948,000 | A | 8/1990 | Grobenkort |
| 4,973,318 | A | 11/1990 | Holm et al. |
| 4,976,701 | A | 12/1990 | Ejlersen et al. |
| 5,000,744 | A | 3/1991 | Hoffman et al. |
| 5,002,537 | A | 3/1991 | Hoffman et al. |
| 5,017,190 | A | 5/1991 | Simon et al. |
| 5,084,017 | A | 1/1992 | Maffetone |
| 5,205,833 | A | 4/1993 | Harsh et al. |
| 5,226,896 | A | 7/1993 | Harris |
| 5,244,465 | A | 9/1993 | Michel |
| 5,269,317 | A | 12/1993 | Bennett |
| 5,286,258 | A | 2/1994 | Haber et al. |
| 5,458,580 | A | 10/1995 | Hajishoreh |
| 5,478,323 | A | 12/1995 | Westwood et al. |
| 5,498,253 | A | 3/1996 | Bonnichsen |
| 5,554,134 | A | 9/1996 | Bonnichsen |
| 5,584,815 | A | 12/1996 | Pawelka et al. |
| 5,611,783 | A | 3/1997 | Mikkelsen |
| 5,693,027 | A | 12/1997 | Hansen et al. |
| 5,743,889 | A | 4/1998 | Sams |
| 5,938,642 | A | 8/1999 | Burroughs et al. |
| 5,954,700 | A | 9/1999 | Kovelman |
| 5,957,896 | A | 9/1999 | Bendek et al. |
| 6,017,330 | A | 1/2000 | Hitchins et al. |
| 6,197,040 | B1 | 3/2001 | LeVaughn et al. |
| 6,582,399 | B1 | 6/2003 | Smith et al. |
| 6,582,408 | B1 | 6/2003 | Buch-Rasmussen et al. |
| 6,648,859 | B2 | 11/2003 | Bitdinger et al. |
| 7,604,619 | B2 | 10/2009 | Eich et al. |
| 2001/0047153 | A1 | 11/2001 | Trocki et al. |
| 2002/0016571 | A1 | 2/2002 | Kirchhofer et al. |
| 2002/0099360 | A1 | 7/2002 | Bierman |
| 2002/0169470 | A1 | 11/2002 | Kuhr et al. |
| 2003/0004466 | A1 | 1/2003 | Bidtiner et al. |
| 2003/0078195 | A1 | 4/2003 | Kristensen et al. |
| 2004/0210199 | A1* | 10/2004 | Atterbury et al. ............ 604/224 |
| 2004/0215152 | A1 | 10/2004 | Kirchhofer et al. |
| 2004/0238776 | A1 | 12/2004 | Peters et al. |
| 2006/0153693 | A1 | 7/2006 | Fiechter et al. |
| 2008/0051713 | A1 | 2/2008 | Kohlbrenner |

FOREIGN PATENT DOCUMENTS

| | | |
|---|---|---|
| CH | 501441 | 1/1971 |
| DE | 2137405 | 2/1973 |
| DE | 4419235 A1 | 12/1995 |
| DE | 20110690 U1 | 9/2001 |
| EP | 217055 | 4/1987 |
| EP | 549694 | 6/1995 |
| EP | 0762311 A2 | 3/1997 |
| EP | 0774270 A1 | 5/1997 |
| EP | 897729 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2214819 | 9/1989 |
| WO | WO92/04926 * | 1/1922 |
| WO | WO 89/02760 | 4/1989 |
| WO | WO 90/09202 | 8/1990 |
| WO | WO 92/04926 | 4/1992 |
| WO | WO 98/47559 | 10/1998 |
| WO | WO 98/56438 | 12/1998 |
| WO | WO 00/02605 | 1/2000 |
| WO | WO00/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO 03/017915 | 3/2003 |
| WO | WO 2006/069456 | 7/2006 |
| WO | WO 2008/009646 | 1/2008 |

OTHER PUBLICATIONS

Search Report from International Application No. PCT/EP2007/062661, mailed Feb. 25, 2008.
English Language Abstract of DE 44 19 235 A1 obtained from Derwent.
English Language Abstract of DE 201 10 690 U1 obtained from Derwent.
English Language Abstract of DE 2137405 obtained from Derwent.
Novo Nordisk product brochure for Insuject-X®, Sep. 1987.
English language machine translation of CH315980 published Sep. 15, 1956.
English language machine translation of FR2026134 (corresponding to patent CH501411, published Jan. 15, 1971).

* cited by examiner

CARTRIDGE AND MEDICAL DELIVERY SYSTEM ACCOMMODATING SUCH CARTRIDGE

CROSS-REFERENCE TO RELATED APPLICATIONS

This application is a continuation of U.S. application Ser. No. 11/784,738 filed Apr. 9, 2007, now abandoned, which is a continuation of U.S. application Ser. No. 10/230,428 filed on Aug. 23, 2002 (published as US 2003-0078195 A1), now abandoned, and claims priority of Danish Application No. PA 2001 01268 filed Aug. 27, 2001 and U.S. Provisional Application No. 60/317,307 filed Sep. 5, 2001,the contents of which are fully incorporated herein by reference.

THE TECHNICAL FIELD OF THE INVENTION

The invention relates to ampoules or cartridges for medical delivery systems. Such cartridges are commonly shaped as a glass or plastic tube being at one end closed by a piston, which may be pressed into the tube to expel the content of the tube at the other end of the tube. This other end is often formed as a bottleneck, the outer end of which may be pierced by a conduit such as an injection needle or a catheter through which the content is expelled.

The invention furthermore relates to a medical delivery system accommodating such a cartridge.

DESCRIPTION OF RELATED ART

Cartridges are widely known for various medical delivery systems. They are especially used for insulin delivery systems, and are usually supplied pre-filled with either 1.5 ml of insulin or 3.0 ml of insulin.

The typical diabetes patient will require a certain amount of insulin either injected or infused into their body every day. The patient loads a cartridge containing the insulin into either an injection system or a pump system and injects or infuses the insulin into their body at a prescribed rate, either through an injection needle or through a catheter having one end inserted into their body. The injection needle or the catheter is at the other end connected to the cartridge. Once the cartridge is empty it is disposed of and a new cartridge is loaded into the delivery system.

Glass is the most preferred material for cartridges containing insulin, however cartridges moulded from plastic such as shown in WO 98.56438 is on the verge of a break through.

A prior art glass cartridge is disclosed in EP 0 549 694. This glass cartridge has an adapter mounted on the distal end of the glass cartridge. The adapter has a bore for receiving the neck part of the glass cartridge, which neck part is closed of by a metal cover. The inner wall of the bore is provided with gripping elements for gripping behind the edge of the metal cover when the neck part is mounted in the bore.

DESCRIPTION OF THE INVENTION

Traditionally, cartridges containing fluid medication have been used with medical delivery systems worldwide for invasive delivery of various types of fluid medicines. However, in typical medical delivery systems a cartridge is simply inserted into the delivery system without the system having any method of determining if the medicament contained in the cartridge is the correct type of medication for that specific delivery system. The user must manually check the cartridge to make sure that the medication is the correct one. This is quit important, since the administration of a incorrect kind of medication or of an incorrect dosage could result in injury or death.

In order to overcome the drawbacks of the prior art it is here suggested to provide the cartridge with a mechanical coding according to claim 1, which mechanical coding has to fit into a specific contour in the medical delivery system in order to allow correct mounting of the cartridge in the medical delivery system.

EXPLANATION OF THE CLAIMS

By providing the cartridge with a mechanical coding it is ensured that the specific cartridge will only fit into a medical delivery system having a cartridge receiving part with a contour conforming to the shape of the mechanical coding of the cartridge.

In some medical delivery systems however, the conduit delivering the medication into the body of the patient are connected directly to the cartridge. The connecting part of the conduit, which are usually referred to as the conduit connector can then be made with an interior contour, which fits over the specific contour of the mechanical coding of the cartridge.

The shape of the contour of the cartridge and the corresponding part of the medical delivery system or the conduit connector can be any geometrical shape wanted, e.g. triangular, square or any other polygon.

In this way the manufacture of the medicament can ensure that a specific medicament contained in a cartridge having a mechanical coding only can be dispensed from a specific medical delivery system and/or through a specific conduit.

The mechanical coding can either be moulded as an integral part of the cartridge, or it can be added to the cartridge in the form of e.g. an adapter, a sleeve or a jacket connected to the cartridge. The mechanical coding could also be provided as a part of the cartridge sealing.

The mechanical coding could also be provided as one or more depressions provided either in the cartridge or in the adapter. The medical delivery system would then be provided with a stud, which has to fit into the depression or depressions in order to allow the cartridge to be connected to the medical delivery system.

When the mechanical coding is made as one or more protrusions extending radial outwards from the outer cartridge surface, which is cylindrical, the cartridge can perform like a key while the cartridge receiving part of the medical delivery system or the conduit connector receiving the cartridge can perform as a key hole.

Instead of providing the outer cartridge surface with the mechanical coding, an adapter carrying the mechanical coding can be mounted on the cartridge at its distal end. This solution is to be preferred for glass cartridges.

When the mechanical coding is made as one or more protrusions extending radial outwards from the outer adapter surface, which is cylindrical, the outer adapter mounted on the cartridge can perform like a key while the cartridge receiving part of the medical delivery system or the conduit connector receiving the cartridge can perform as a key hole.

By letting the protrusion or protrusions located on the outer surface of the cartridge or the adapter form a substantial circular protrusion, the outer surface of either the cartridge or the adapter can be made rotational symmetrical.

The protrusions can be formed as one circular protrusion covering substantially 360 degrees of the outer surface, or as a number of individual protrusions preferably located along a circle on the outer periphery of the outer surface of the cartridge or the adapter, such that the outer surface is rotational symmetrical, hence the location of the cartridge or the adapter in relation to the cartridge receiving part of the medical delivery system or the conduit connector receiving the cartridge is of importance.

The mating key hole of the cartridge receiving part of the medical delivery system or the conduit connector needs in its simplest form just be a hole having an inside contour conforming to the outside diameter of the circular protrusion.

Cartridges can then be made to fit specific delivery systems simply by mating the outside diameter of the circular protrusion with the inside contour of the cartridge receiving part of the medical delivery system or with the inside contour of the conduit connector.

The circular protrusion can either be made as one or a few protrusions substantially covering 360 degrees of the outer cartridge surface or the outer adapter surface, or it can be made as a number of raised islands located along the outer cartridge surface or the outer adapter surface. The number of raised island can vary from one and up.

The diameter of the circular protrusion can be utilized to indicate a parameter of the medicament contained in the specific cartridge. The parameter could e.g. be the type of medicament or it could be the concentration of the medicament.

When the cartridge contains insulin for treating diabetes it is to be preferred that the specific diameter of the circular protrusion is dedicated a specific concentration of insulin. Most insulin sold today has a concentration of 100 International Units (IU) pr. milliliter of insulin. Recently insulin with a concentration of 200 IU pr. ml. has emerged.

If a patient by accident loads a cartridge containing insulin with a concentration of 200 IU pr. ml. into a medical delivery system which are designed for use with insulin having a concentration of 100 IU pr. ml the patient will inject twice the number of International Units needed while the medical delivery systems normally are designed to expel a given quantity of insulin. The consequences of this could be fatal.

It is therefore of the outmost importance that cartridges containing insulin with a concentration of 200 IU pr. ml are effectively prevented from being used in medical delivery systems designed to handle insulin with 100 IU pr. ml.

This is done by providing cartridges containing insulin with a concentration of 200 IU pr. ml. with a circular protrusion with a larger diameter than a cartridge containing insulin with only 100 IU pr. ml. When at the same time the inside contour of the cartridge receiving part of the medical delivery system or the conduit connector for a 100 IU pr. ml system is made to fit the diameter of the circular protrusion of the adapter of a cartridge containing insulin with a 100 IU pr. ml, it is ensured that a cartridge containing insulin with a concentration of 200 IU pr. ml can not be used in such a delivery system while the diameter of the circular protrusion of this cartridge is to large to fit into the inside contour of the cartridge receiving part of the medical delivery system or the conduit connector of a 100 IU pr. ml system.

This system can be expanded to also encompass insulin with even higher concentrations, such as 300 or 400 IU pr. ml simply by moulding the circular protrusions carried on the cartridges of these higher concentrations with larger diameters, such that the circular protrusion of a cartridge containing insulin with a specific concentration do not fit into the cartridge receiving part of a medical delivery system and/or into a conduit connector for a medical delivery system designed for a lower concentration of insulin.

When using cartridges with circular protrusions with larger diameters for higher concentrations of insulin it will however be possible for a patient to fit a cartridge containing insulin with a lower concentration into the cartridge receiving part of a medical delivery system and/or into a conduit connector of system designed for a higher concentration of insulin. The result of this is that the patient does not get insulin enough for the correct treatment, which is a major inconvenience for that individual patient, but which is not a fatal incident, and which the patient will discover next time the blood glucose level is measured.

It is furthermore an object of the present invention to provide a medical delivery system accommodating a cartridge carrying a mechanical coding.

Such a medical delivery system may have a housing for accommodating a cartridge with an inside shape conforming to the outside shape of the mechanical coding, such that only cartridges that are suitable for use with the medical delivery system are capable of being received by the medical delivery system.

In some medical delivery systems, the conduit delivering the fluent medicament is connected directly to the cartridge by use of a conduit connector located at one end of the conduit. This conduit connector will then have a contour conforming to the mechanical coding on the outer cartridge surface or the adapter surface, such that only cartridges containing a fluid medicament suitable for the specific medical delivery system can be connected to the conduit of that specific medical delivery system.

The medicament contained in the cartridge is preferably insulin, the mechanical coding is a circular protrusion and the specific outside diameter of the circular protrusion is dedicated a specific concentration of insulin and the outside diameter is chosen as a larger diameter for a higher concentration.

In this way it is ensured that only insulin with concentrations suitable for or lower than the insulin concentration a specific insulin delivery system or conduit is designed for can actually be used in that specific insulin delivery system or with that specific conduit.

DEFINITIONS

In the present context, the term "Medical delivery system" is taken to mean any system for invasive bringing a fluid medicament into a human body. The most commonly used medical delivery system is an injection system or an infusion system. In an injection system a predetermined quantity of the medicament are brought into the human body at one time through a conduit such as an injection needle temporarily inserted in the body. In an infusion system a quantity of the medicament is pumped via a pump system into the human body at a small constant rate through a conduit such as a catheter constantly inserted in the human body.

Although the wording "human body" is used through out this application, the medical delivery system could as well be used on any other mammal body without dispersing from the scope of the claims.

It is to be understood that the wording "protrusion", refers to an element or a part that protrudes from a surface disregarding the form or the shape of the element or the part, while the term "circular protrusion" refers to a part which continuously protrudes from a circular surface substantially at all 360 degrees round the surface. The circular protrusion can however be made from a number of raised points located at a circle at the periphery of the surface without dispersing from the scope of the claims.

In the present context, the term "Conduit connector" is taken to mean a part or an element which is connected to the conduit or moulded as an integral part of the conduit, and which can be connected directly to either the cartridge, to the adapter or to the medical delivery system.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Initially it may be convenient to define that, the term "distal end" of the cartridge 2 or the adapter 1 is meant to refer to the end carrying the conduit through which the medicine is expelled, whereas the term "proximal end" is meant to refer to the opposite end.

Figure 1:
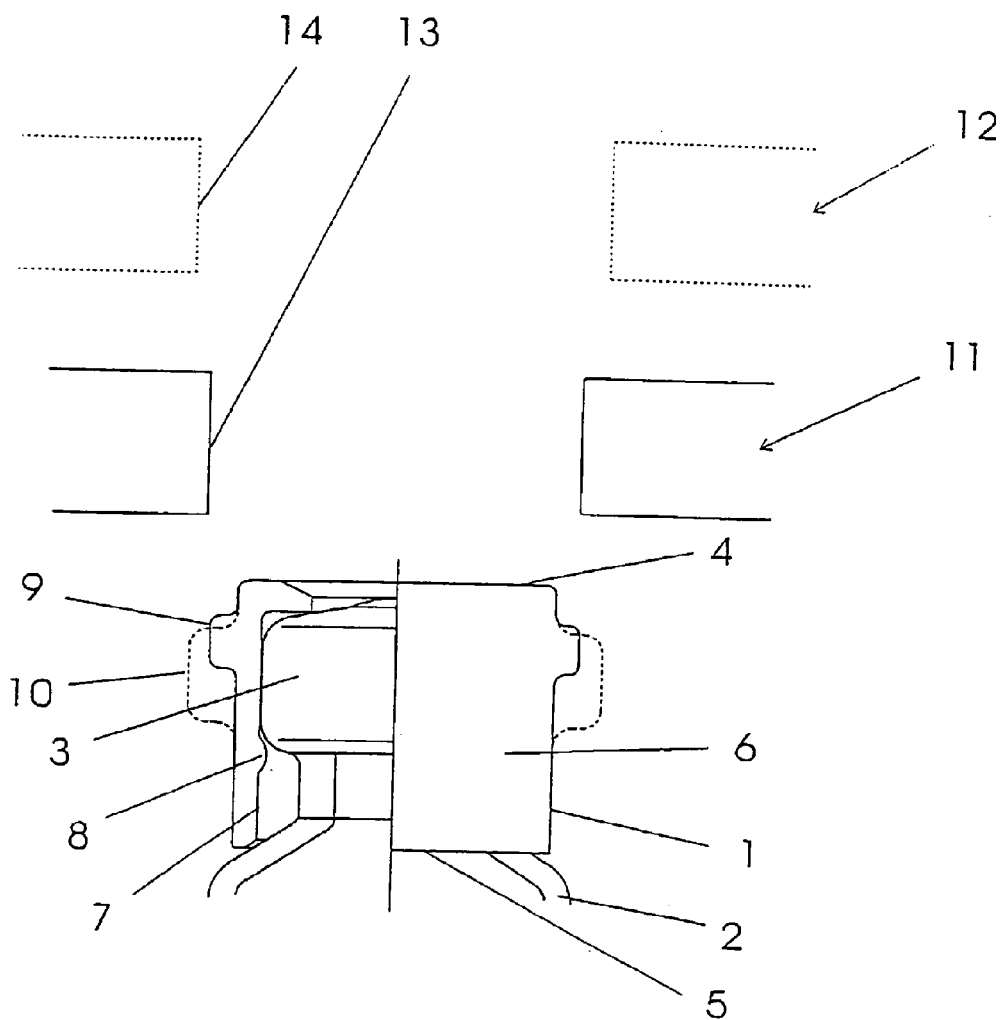
FIG. 1 Shows an adapter mounted on a cartridge.

FIG. 1 shows the adapter 1 mounted on a cartridge 2. The cartridge 2 is closed of by a metal cover 3 which are folded over the bottleneck of the cartridge 2 and beaded at the lower edge. The adapter 1 has a distal end surface 4, a proximal end surface 5 and an outer adapter surface 6 there between. The adapter 1 further has a longitudinal bore conforming the outer diameter of the metal cover 3. The adapter 1 is mounted on the cartridge 2 simply by pushing the adapter 1 over the metal cover 3. This is possible since the inside bore of the adapter has a diameter larger than the outside diameter of the metal cover 3. The inside surface 7 of this bore is provided with a number of gripping elements 8, usually there are three such gripping elements 8 located with a 120 degrees displacement. The diameter formed by these three gripping elements 8 are smaller than the diameter of the metal cover 3, such that the gripping elements 8 will grip behind the beaded end of the metal cover 3 when the adapter 1 is mounted on the cartridge 2.

Figure 2:
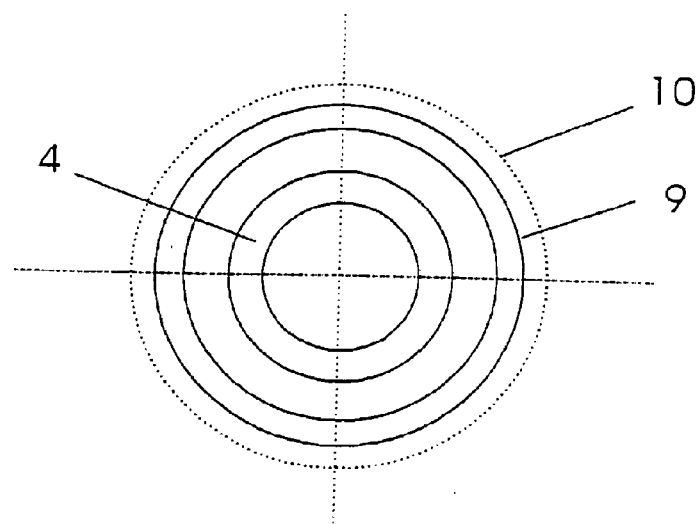
FIG. 2 Shows the adapter of FIG. 1 seen from above

The outer adapter surface 6 is provided with one or more protrusions 9, which protrusion 9 extends radial outwards from the outer adapter surface. The protrusion 9 can as shown in FIG. 2 have a circular form covering 360 degrees of the outer adapter surface 6.

The circular protrusion 9 has an outer diameter, which can be different from one adapter 1 to another adapter 1 as indicated with dotted lines 10.

The cartridge receiving part 11 is provided with a circular bore 13, which receives the adapter 1 when the cartridge 2 is mounted in the cartridge receiving part 11. For other types of cartridge receiving parts 12 indicated with dotted lines, the bore 14 could have a different diameter.

Figure 6:
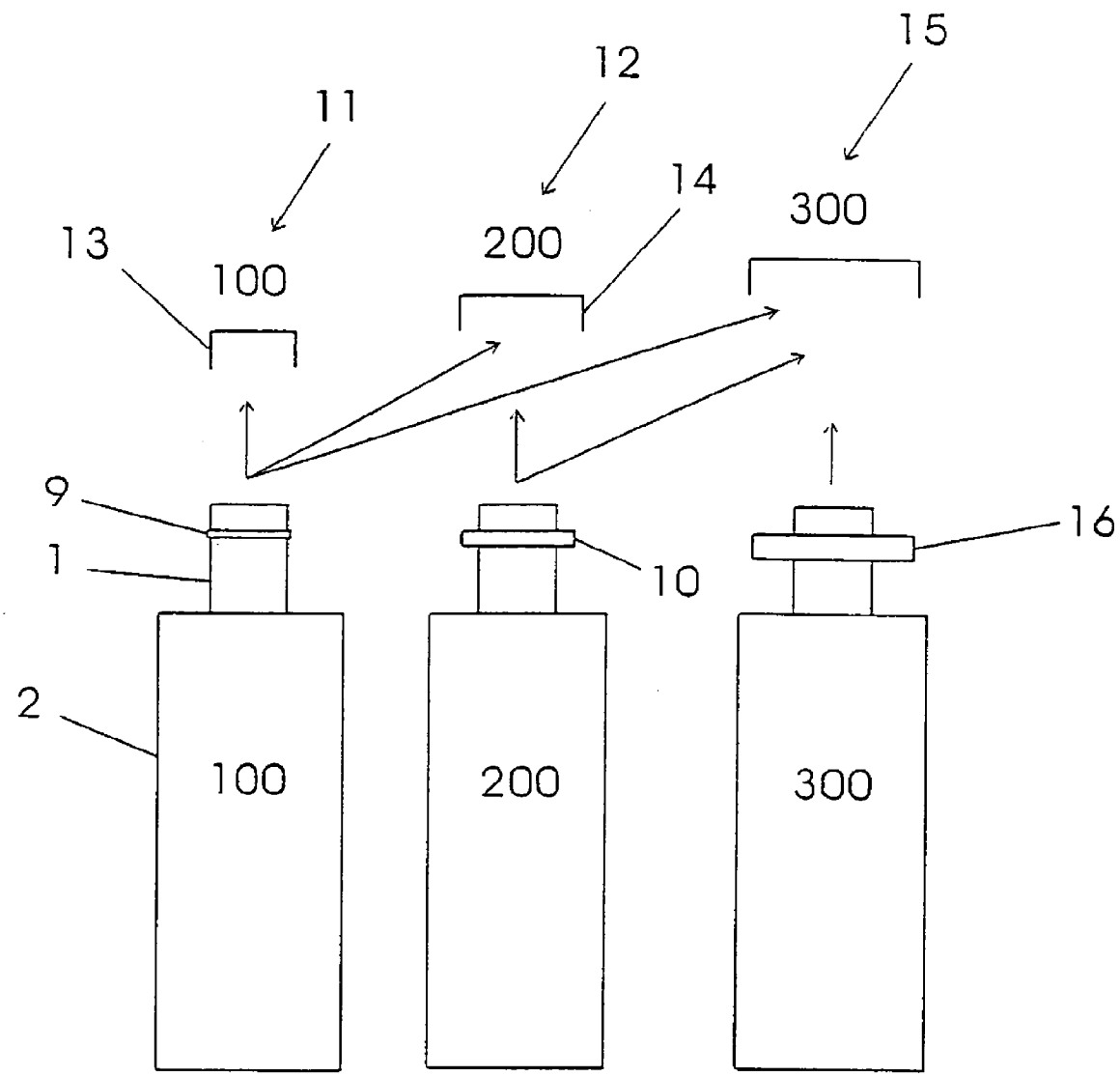
FIG. 6 Shows an adapter, which can be horizontally mounted on the cartridge.

Referring to FIGS. 1 and 6, a specific outside diameter of the circular protrusion 9, 10 is dedicated to a specific concentration of the insulin contained in the cartridge 2. The cartridge 2 containing the lowest concentration is provided with an adapter 1 having only a small outside diameter of the circular protrusion 9, while the larger concentrations are provided with an adapter 1 having a larger diameter of the circular protrusion 10.

The same is the case for the diameter of the bore of the cartridge receiving part 11. The cartridge receiving part 11 on a medical delivery system designed for low concentrations has the smallest diameter of the bore 13, while the cartridge receiving part 12 on a medical delivery system for handling larger concentrations has a larger bore 14.

As illustrated in FIG. 6 a cartridge receiving part 11 on a medical delivery system designed for 100 IU pr. ml can only receive the adapter 1 of an cartridge 2 containing insulin with a 100 IU pr. ml. concentration, which is indicated by the outside diameter of the circular protrusion 9, while the cartridge receiving part 12 on a system designed for 200 IU pr. ml. can receive both the adapter 1 of a cartridge 2 containing insulin with a concentration of 100 IU pr. ml and the adapter 1 of a cartridge 2 containing insulin with a concentration of 200 IU pr. ml, indicated by a circular protrusion 10 having a larger outside diameter.

Although the 100 IU cartridge 2 of FIG. 6 is described as being a cartridge 2 with an adapter 1 mounted thereto, it could as well be a cartridge 2 moulded from plastic with the protrusion 9 moulded as an integral part of the cartridge 2.

The cartridge receiving part 15 of medical delivery system designed for 300 IU pr. ml is able of handle both the previous mentioned adapters 1 having circular protrusions 9, 10 as well as an adapter of a cartridge having a circular protrusion 16 with an even larger diameter containing insulin with a concentration of 300 IU pr. ml.

Figure 3:
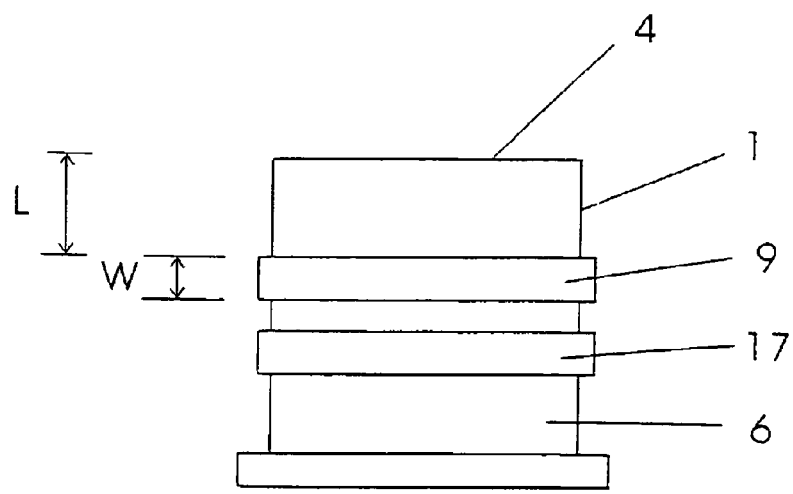
FIG. 3 Shows an adapter with two circular protrusions protruding from the outer adapter surface.
Figure 4:
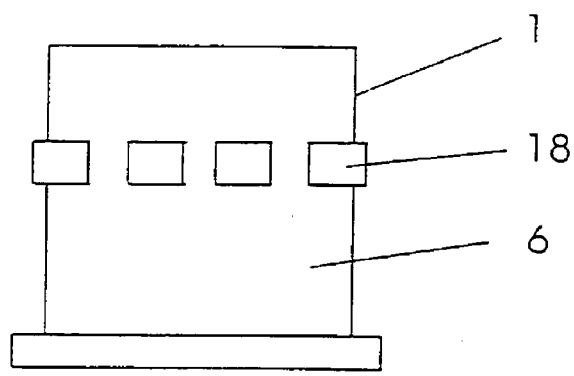
FIG. 4 Shows an adapter with a number of raised islands protruding forming the outer adapter surface.
Figure 5:
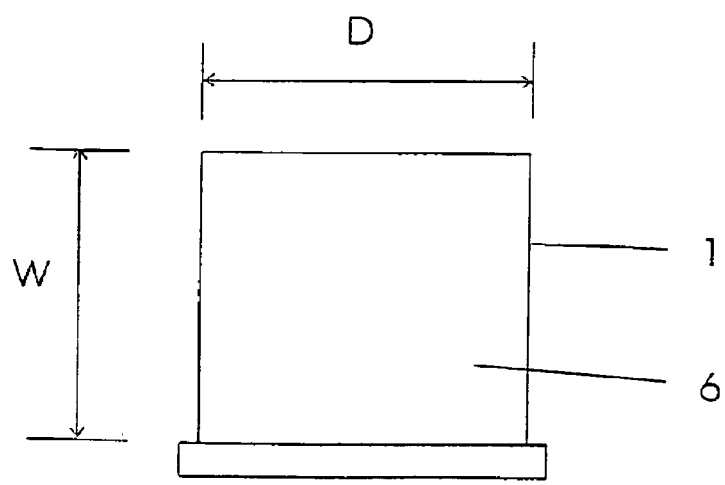
FIG. 5 Shows an adapter where the protrusion has the same width as the extension of the outer adapter surface.

FIG. 3 to 5 show different configurations of adapters 1. The adapter 1 of FIG. 3 is provided with two protrusions 9, 17 both covering 360 degrees of the outer surface 6. The first protrusion 9 is shown as having a width W.

The adapter 1 shown in FIG. 4 is provided with a number of protrusions 18 which are shaped as a number of raised points, and which raised points are provided on a circle covering substantially 360 degrees of the outer surface 6 of the adapter 1.

The circular protrusion or protrusions can have a width W that equals the longitudinal extension of the outer adapter surface 6 as shown in FIG. 5, in which case there in fact is no protrusions but simply a relatively large diameter D of the entire outer adapter surface 6.

The circular protrusion 9 shown in FIG. 3 is located in a specific distance L from the distal end surface 4. Instead of providing the circular protrusion 9 with different diameters, the general idea of the present invention could also be realised by providing the circular protrusion 9 in different distances L from the distal end surface 4 for different insulin concentrations. It is apparent that only one circular protrusion 9 is needed in this case. The distance L could e.g. be chosen as a little distance for an insulin with a concentration of 200 IU pr. ml. and a greater distance for an insulin with a concentration of 100 IU pr. ml. The cartridge receiving part 11, 12 of the medical delivery system could then be made with an inside located neck or shoulder with a narrow diameter preventing the cartridge 2 containing insulin with a concentration on 200 IU pr. ml. to fully enter the cartridge receiving part of a medical deliver system designed for insulin with a concentration on 100 IU pr. ml.

Some preferred embodiments have been shown in the foregoing, but it should be stressed that the invention is not limited to these, but may be embodied in other ways within the subject matter defined in the following claims.

The invention claimed is:

1. A medication delivery system for delivering medication from a cartridge, the medication delivery system comprising:
   a medication delivery device that is calibrated and designed for a specific concentration of a medication and wherein the medication delivery device has a cartridge receiving portion with a shape and diameter so that the medication delivery device is structured to accept only cartridges having a specific mechanical coding that corresponds to the concentration for which the device is designed and calibrated, or a lower concentration;
   a cartridge containing one of a plurality of different concentrations of medication, the cartridge containing at least one mechanical coding selected from a plurality of mechanical codings, the mechanical coding(s) comprising at least one circular element(s) shaped as a substantially continuous circumferential protrusion having a circular cross section when viewed in a cross section transverse to the longitudinal axis of the cartridge and the protrusion extending radially outward from a cylindrical portion of the cartridge and having a diameter with a predetermined value and a predetermined shape that allows the cartridge to fit into the cartridge receiving portion of the medication delivery device and wherein the cartridge is structured to be axially insertable into a medication delivery device in any rotational orientation; and
   wherein the selected mechanical coding(s) allow(s) the cartridge to be used only in a delivery device designed and calibrated for the concentration indicated by the selected mechanical coding(s), or a lower concentration, wherein the mechanical coding(s) comprise protrusion(s) having different diameter(s) and/or different length L from a distal surface, and
   wherein cartridges having a higher concentration of medication than which the device is designed and calibrated for are not insertable into the medication delivery device.

2. The medication delivery system of claim 1, wherein the medication is insulin and the medication delivery system is an injection device and wherein at least one of the mechanical codings is indicative of 100 IU per ml insulin and wherein the medication delivery device is designed and calibrated for 100 IU per ml medications and wherein the cartridge receiving portion of the medication delivery device accepts cartridges having the mechanical coding thereby allowing only specific cartridges containing 100 IU per ml concentrations to be inserted and used with the medication delivery system.

3. The medication delivery system of claim 2, wherein at least one of the mechanical codings is indicative of an insulin having a concentration of something other than IU 100 insulin.

4. The medication delivery system of claim 1, wherein each diameter size corresponds to a specific concentration.

5. The medication delivery system of claim 1, wherein a larger diameter mechanical coding is indicative of a higher concentration of the medicament adapted to be stored in the cartridge.

6. A cartridge comprising:
   a medication storing portion suitable for use in a medication delivery device, wherein the medication storing portion of the cartridge is adapted to store a medicament that is available in a plurality of concentrations;
   at least one mechanical coding comprising at least one circular element(s) shaped as a substantially continuous circumferential protrusion(s) when viewed in a cross section transverse to the longitudinal axis of the cartridge, the circular element(s) having a diameter and extending radially outwards from a cylindrical portion of the cartridge and wherein at least the diameter of the circular element mechanical coding(s) are indicative of a specific concentration of the medicament and wherein the mechanical coding is structured to allow the cartridge to be used only in medication delivery devices that are configured to mechanically accept the circular element mechanical coding(s) and the cartridge, and the cartridge having a higher concentration of medication than which a medication delivery device is designed and calibrated for is not insertable into the medication delivery device.

7. A cartridge according to claim 6, wherein the cartridge having an outer surface being is generally cylindrical and the at least one selected mechanical coding comprises a protrusion having a specific diameter and shape that allows the cartridge to be inserted and used only in specific medication delivery devices that are designed and calibrated for 100 IU per ml concentrations.

8. A cartridge according to claim 7, wherein the medicament comprises an insulin.

9. A cartridge according to claim 6, wherein the medicament is an insulin.

10. A cartridge according to claim 9, wherein the at least one mechanical coding is on an adapter that is disposed on an outer cylindrical wall of the cartridge wherein the adapter is in the form of a sleeve that jackets at least the medicaton storing portion of the cartridge and wherein the mechanical coding has a circular cross section.

11. A cartridge according to claim 6, wherein a larger diameter mechanical coding is indicative of a higher concentration of the medicament adapted to be stored in the medication storing portion.

12. A medication cartridge adapted for use with a medication delivery device, the cartridge comprising:
   a body having a cylindrical wall around a medication storing compartment;
   a medication selected from a group of medications suitable for delivery with the medication delivery device and stored in the medication storing compartment; and
   a mechanical coding; wherein the mechanical coding comprises at least one circular element(s) shaped as a substantially continuous protrusion having a circular cross section when viewed in a cross section transverse to the longitudinal axis of the cartridge and extending circumferentially and radially with respect to the cylindrical wall;
   wherein the mechanical coding is indicative of the specific type of medication in the cartridge, and allows the cartridge to be used only in a medication delivery device configured to mechanically accept the mechanical coding and the cartridge, and
   wherein a cartridge having a higher concentration of medication than which the medication delivery device is designed and calibrated for is not insertable into the medication delivery device.

13. The medication cartridge of claim 12, wherein the specific type of medication is a 100 IU per ml concentration of medication.

14. The medication cartridge of claim 12, wherein the mechanical coding is integral with the cylindrical wall of the cartridge.

15. The medication cartridge of claim 12, wherein the mechanical coding is located a distance L from a distal end of the cartridge so that the mechanical coding is located between a distal and a proximal end of the cartridge body and wherein the coding has a diameter D that is larger than the diameter of the cylindrical wall of the body.

16. The medication cartridge of claim 12, wherein the protrusion that forms the mechanical coding is located on an adapter sleeve that jackets the cylindrical wall.

17. The medication cartridge of claim 16, wherein the mechanical coding is structured to align the cartridge axially within a cartridge receiving portion of one or more medication delivery device that have been determined in advance to be suitable for use with the medication in the cartridge.

18. The medication cartridge of claim 17, wherein the medication is an insulin and wherein the mechanical coding has a shape complimentary to the shape of the cartridge receiving portion.

19. The medication cartridge of claim 12, wherein a larger diameter mechanical coding is indicative of a higher concentration of the medicament adapted to be stored in the medication storing compartment.

20. A method of using a medication delivery system for delivering medication from a cartridge, the method comprising:
   providing a medication delivery device that is calibrated and designed for a specific concentration of a medication and wherein the medication delivery device has a cartridge receiving portion with a shape and diameter so that the medication delivery device is structured to accept only cartridges having a specific mechanical coding that corresponds to the concentration for which the device is designed and calibrated, or a lower concentration;
   providing a cartridge containing one of a plurality of different concentrations of medication, the cartridge containing at least one mechanical coding selected from a plurality of mechanical codings, the mechanical coding(s) comprising at least one circular element(s) shaped as substantially continuous circumferential protrusion having a circular cross section when viewed in a cross section transverse to the longitudinal axis of the cartridge and the protrusion extending radially outward from a cylindrical portion of the cartridge and having a diameter with a predetermined value and a predetermined shape that allows the cartridge to fit into the cartridge receiving portion of the medication delivery device and wherein the cartridge is structured to be axially insertable into a medical delivery device in any rotational orientation; and
   wherein the selected mechanical coding(s) allow(s) the cartridge to be used only in a medication delivery device designed and calibrated for the concentration indicated by the selected mechanical coding(s), or a lower concentration, wherein the mechanical coding(s) comprise protrusion(s) having different diameter(s) and/or different length L from a distal surface, and
   wherein cartridges having a higher concentration of medication than which the device is designed and calibrated for are not insertable into the medication delivery device.

* * * * *